United States Patent
Simpson et al.

(10) Patent No.: US 8,382,935 B2
(45) Date of Patent: Feb. 26, 2013

(54) RAPID EXCHANGE BALLOON CATHETER HAVING A REINFORCED INNER TUBULAR MEMBER

(75) Inventors: John A. Simpson, Carlsbad, CA (US); Jessie Delgado, Murrietta, CA (US); Robert Alcantara, Temecula, CA (US); Jason Phillips, Hemet, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 1424 days.

(21) Appl. No.: 11/679,701

(22) Filed: Feb. 27, 2007

(65) Prior Publication Data

US 2007/0151650 A1    Jul. 5, 2007

Related U.S. Application Data

(62) Division of application No. 10/335,489, filed on Dec. 31, 2002, now Pat. No. 7,195,611.

(51) Int. Cl.
  *B29C 65/02* (2006.01)
  *A61M 25/00* (2006.01)

(52) U.S. Cl. .......................... 156/296; 156/211; 156/293

(58) Field of Classification Search .................. 156/189, 156/196, 198, 211, 256, 293, 296, 423, 510, 156/513, 581
  See application file for complete search history.

(56) References Cited

U.S. PATENT DOCUMENTS

| | | | |
|---|---|---|---|
| 5,061,273 A | 10/1991 | Yock | |
| 5,156,594 A * | 10/1992 | Keith | 604/103.09 |
| 5,328,472 A * | 7/1994 | Steinke et al. | 604/102.02 |
| 5,425,711 A | 6/1995 | Ressemann et al. | |
| 5,470,315 A * | 11/1995 | Adams | 604/103.09 |
| 5,743,875 A * | 4/1998 | Sirhan et al. | 604/96.01 |
| 6,004,310 A | 12/1999 | Bardsley et al. | |
| 6,030,405 A | 2/2000 | Zarbatany et al. | |
| 6,117,106 A | 9/2000 | Wasicek et al. | |
| 6,179,810 B1 | 1/2001 | Wantink et al. | |
| 6,180,367 B1 | 1/2001 | Leung et al. | |
| 6,190,358 B1 * | 2/2001 | Fitzmaurice et al. | 604/103.04 |
| 6,193,686 B1 | 2/2001 | Estrada et al. | |
| 6,264,671 B1 * | 7/2001 | Stack et al. | 606/198 |
| 6,548,010 B1 * | 4/2003 | Stivland et al. | 264/482 |
| 6,610,068 B1 | 8/2003 | Yang | |
| 6,733,486 B1 | 5/2004 | Lee et al. | |
| 6,929,635 B2 | 8/2005 | Shelso | |
| 2003/0105427 A1 | 6/2003 | Lee et al. | |

OTHER PUBLICATIONS

Finding the Cure for Epoxy Dispensing Frustrations Adhesives, Sealants, and Coatings www.ecmag.com Dec. 15, 2001 By Ken Harvill http://www.multi-seals.com/ecn.php?id=adhesivefilm.*
Merriam Websters Collegiate Dictionary 1997, Merriam-Webster, Incorporated ISBN 0-87779-709-0 p. 880.*

* cited by examiner

*Primary Examiner* — Richard Crispino
*Assistant Examiner* — Martin Rogers
(74) *Attorney, Agent, or Firm* — Fulwider Patton LLP (57) ABSTRACT

A balloon catheter including an elongated shaft having an inflation lumen, a guidewire lumen, a proximal shaft section, and a distal shaft section with a balloon on the distal shaft section, the distal shaft section formed by an outer tubular member having an opening in a sidewall, and an inner tubular member having a distal portion in the outer tubular member and a proximal portion extending through the sidewall opening and along an outer surface of a portion of the outer tubular member located proximal to the sidewall opening, with polymeric filler material around the outer surface of at least the proximal portion of the inner tubular member. The inner tubular member preferably comprises a polymeric tube having a reinforcing coiled member embedded therein. Preferably, a crescent shaped portion of the inflation lumen extends along side the proximal portion of the inner tubular member.

3 Claims, 4 Drawing Sheets

RAPID EXCHANGE BALLOON CATHETER HAVING A REINFORCED INNER TUBULAR MEMBER

This application is a division of currently pending U.S. patent application Ser. No. 10/335,489 filed Dec. 31, 2002.

BACKGROUND OF THE INVENTION

This invention relates generally to catheters, and particularly, to intravascular catheters for use in percutaneous transluminal coronary angioplasty (PTCA) or the delivery of stents.

In percutaneous transluminal coronary angioplasty (PTCA) procedures, a guiding catheter is advanced in the patient's vasculature until the distal tip of the guiding catheter is seated in the ostium of a desired coronary artery. A guidewire is first advanced out of the distal end of the guiding catheter into the patient's coronary artery until the distal end of the guidewire crosses a lesion to be dilated. A dilatation catheter, having an inflatable balloon on the distal portion thereof, is advanced into the patient's coronary anatomy over the previously introduced guidewire until the balloon of the dilatation catheter is properly positioned across the lesion. Once properly positioned, the dilatation balloon is inflated with inflation fluid one or more times to a predetermined size at relatively high pressures so that the stenosis is compressed against the arterial wall and the wall expanded to open up the vascular passageway. Generally, the inflated diameter of the balloon is approximately the same diameter as the native diameter of the body lumen being dilated so as to complete the dilatation but not overexpand the artery wall. After the balloon is finally deflated, blood resumes through the dilated artery and the dilatation catheter and the guidewire can be removed therefrom.

In such angioplasty procedures, there may be re-stenosis of the artery, i.e. reformation of the arterial blockage, which necessitates either another angioplasty procedure or some other method of repairing or strengthening the dilated area. To reduce the restenosis rate of angioplasty alone and to strengthen the dilated area, physicians now normally implant an intravascular prosthesis, generally called a stent, inside the artery at the site of the lesion. Stents may also be used to repair vessels having an intimal flap or dissection or to generally strengthen a weakened section of a vessel or to maintain its patency. Stents are usually delivered to a desired location within a coronary artery in a contracted condition on a balloon of a catheter which is similar in many respects to a balloon angioplasty catheter and expanded within the patient's artery to a larger diameter by expansion of the balloon. The balloon is deflated to remove the catheter and the stent left in place within the artery at the site of the dilated lesion.

In rapid exchange type balloon catheters, the catheter has an inflation lumen extending from the proximal end of the catheter to a balloon on a distal shaft section, a distal guidewire port at the distal end of the catheter, a proximal guidewire port located distal to the proximal end of the catheter, and a relatively short guidewire lumen extending therebetween. One difficulty has been forming a rapid exchange junction at the proximal guidewire port which is flexible, yet kink resistant and rugged, while maintaining collapse resistance. Some conventional designs have employed reinforcing layers or stiffening wires bridging the rapid exchange junction to prevent kinking at the junction between the proximal and distal sections. Reinforcing coils embedded in the polymeric tubular members of the shaft, such as for example in an inner tubular member defining a guidewire lumen, provide increased collapse resistance. Despite these attempts, prior art designs have suffered from various drawbacks. For example, one difficulty has been preventing embedded reinforcing coils from protruding through the polymeric layers of the shaft tubular member during assembly of the shaft. Accordingly, it would be a significant advance to provide a catheter having an improved catheter shaft junction between shaft sections such as the proximal and distal shaft sections. This invention satisfies these and other needs.

SUMMARY OF THE INVENTION

The invention is directed to a balloon catheter including an elongated shaft having an inflation lumen, a guidewire lumen, a proximal shaft section, and a distal shaft section with a balloon on the distal shaft section, with the distal shaft section being formed by an outer tubular member, and an inner tubular member having a distal portion in the outer tubular member and a proximal portion extending through a sidewall of the outer tubular member and along an outer surface of a portion of the outer tubular member. Polymeric filler material extends at least partially around the outer surface of the inner tubular member and extending along at least the proximal portion of the inner tubular member. The inner tubular member preferably comprises a polymeric tube having a reinforcing coiled member embedded therein, and defines the guidewire lumen. Preferably, a crescent-shaped portion of the inflation lumen extends along side the proximal portion of the inner tubular member. The resulting rapid exchange junction of the catheter at the proximal guidewire port has an improved low profile configuration which provides kink resistance and which prevents or inhibits the coiled reinforcing member from breaking through the polymeric tube of the inner tubular member during assembly or use of the catheter.

In a presently preferred embodiment, the balloon catheter of the invention generally comprises an elongated shaft having a proximal end, a distal end, an inflation lumen extending from the proximal end to a location proximal of the distal end of the shaft, and a guidewire lumen extending from a location distal of the proximal end to the distal end of the shaft. The proximal shaft section comprises a proximal tubular member having a proximal end, a distal end, and defining a proximal section of the inflation lumen. The distal shaft section outer tubular member has a proximal end secured to a distal end of the proximal shaft section, and has a distal end, and defines a distal section of the inflation lumen in fluid communication with the proximal section of the inflation lumen. The guidewire lumen defined by the inner tubular member is in fluid communication with a guidewire distal port at the distal end of the catheter, and a guidewire proximal port distal to the proximal shaft section.

The inner tubular member preferably has a coiled reinforcing member, which typically comprises a helically or spirally coiled member such as a flat ribbon or a round wire. In a presently preferred embodiment, the inner tubular member comprises a multi-layered polymeric tube heat shrunk down onto the coiled member, to embed the coiled member therein, although a variety of suitable coil supported tubular members may be used as are conventionally known.

The rapid exchange junction at the proximal guidewire port has a low profile provided in part by the thin wall thickness of the inner tubular member, yet with sufficiently high rupture pressure and kink resistance. During assembly of the shaft, the proximal portion of the inner tubular member, which is generally in a side-by-side relationship with a proximal portion of the outer tubular member, is bonded to the outer surface of the outer tubular member by applying heat, and typically, applying radially inward force, for example, with heat shrink tubing to cause the polymeric materials to soften and typically flow. To keep the inflation lumen and the guidewire lumen open during the heat bonding, one mandrel is positioned in the outer tubular member and another mandrel is in the inner tubular member. Disadvantageous thinning of the wall of the inner tubular member which would otherwise occur during the heat bonding is minimized in the catheter of the invention, due at least in part to providing a crescent-shaped mandrel in the inflation lumen during assembly of the shaft. The crescent-shaped mandrel has a concave surface that matches the contour of the inner tubular member's outer surface, and a convex surface that matches the contour of the outer tubular member's inner surface. The convex surface provides a relatively large area of contact with the inner tubular member as compared to the essentially line contact between a pair of round mandrels which avoids pinching the softened polymeric material between the two mandrels in the inner and outer tubular members. The portion of the inflation lumen extending along side the proximal portion of the inner tubular member thus is formed with a crescent shape corresponding to the crescent shape of the mandrel therein during the heat bonding of the rapid exchange junction at the proximal guidewire port. The crescent shaped mandrel is removed from the catheter after assembly of the catheter is complete and before use of the catheter.

The crescent shaped mandrel and resulting crescent shaped inflation lumen have a generally C-shaped transverse cross sectional shape, similar to a quarter moon shape. Preferably, the crescent shaped mandrel, provided in the inflation lumen during catheter assembly, has concave and convex surfaces which meet with a rounded-off configuration, and not a sharply pointed configuration, to avoid damaging the tubular members during assembly. The inflation lumen proximal and distal to the crescent-shaped portion can have a variety of suitable shapes such as a circular, oblong/oval, D-shaped or C-shaped transverse cross-section, and typically has a circular and/or annular shape.

The proximal portion of the inner tubular member (i.e., the portion of the inner tubular member extending along the outer surface of the outer tubular member) is reinforced with polymeric filler material. The filler material preferably extends at least partially around an outer surface of the inner tubular member so that it is in contact with at least a part of the circumference of the inner tubular member along the proximal portion thereof, to prevent or inhibit the coiled reinforcing member from breaking through the polymeric tube during assembly or use of the catheter. In a presently preferred embodiment, the filler material extends completely around and in contact with the inner tubular member. In an alternative embodiment, the filler material extends around the inner and outer tubular members, so that it partially extends around the inner tubular member and partially extends around the outer surface of the outer tubular member. The filler material is typically applied during catheter assembly as a tube configured to be positioned around the proximal portion of the inner tubular member, or around both the inner and outer tubular members, prior to bonding thereof. The polymeric material of this filler tube softens and flows during bonding of the inner tubular member proximal portion to the outer tubular member at the guidewire proximal port. The polymeric filler material thus provides an additional layer of material which preferably serves as a supply of hot-melt adhesive to prevent the coiled reinforcing member from breaking through the sidewall and/or the end of the inner tubular member, and to bond the members together at least in the embodiment in which it extends completely around and in contact with the inner tubular member. The resulting rapid exchange junction configuration, having the proximal portion of the inner tubular member along side a crescent shaped portion of the inflation lumen and reinforced with filler material, can be used in a variety of catheter designs and is especially useful for a catheter having a thin walled inner tubular member requiring reinforcement. Additionally, the rapid exchange junction preferably has a circular outer surface, with a lower profile than would otherwise be provided if the tubular members took on an oval or figure-eight configuration during fusion bonding.

The filler material tube has a length preferably at least extending along the entire proximal portion of the inner tubular member, with a proximal end at or extending proximally beyond the proximal end of the inner tubular member. In one embodiment, the polymeric filler material tube has a length which is longer than the proximal portion of the inner tubular member, to thereby cover the proximal end of the inner member where the coil terminates, by extending proximally beyond the proximal end of the embedded coil. However, a variety of suitable configurations may be used, including having the coil proximal end terminate distal to the proximal end of the inner tubular member to minimize coil breakthrough at the proximal end of the inner tubular member, provided the collapse resistance of the nonreinforced portion of the inner tubular member is sufficiently high. The distal end of the filler material is typically located adjacent to the distal end of the proximal portion of the inner tubular member, although it may alternatively extend along all or part of the distal portion of the inner tubular member within the outer tubular member lumen. Additionally, the polymeric filler material may have colorant to thereby facilitate observation of the guidewire proximal port by the operator during use of the catheter and avoid the need for a separate marker at the guidewire proximal port.

A variety of suitable polymeric materials may be used for the polymeric filler material depending on the nature of the polymeric materials forming the outer surfaces of the inner and outer tubular members of the shaft. The melt temperature of the polymeric filler material is typically sufficiently low to melt and flow during heat bonding. In one embodiment, the polymeric filler material is selected from the group consisting of a polyether block amide (PEBAX), a nylon, a polyurethane, or an adhesive polymer such as the ethylene-based adhesive PRIMACOR. Similarly, in one embodiment, the polymeric materials forming at least an outer surface of a proximal portion of the inner and outer tubular members are selected from the group consisting of PEBAX, nylon, and polyurethane, although a variety of suitable polymeric materials, different from or the same as the filler polymeric material and useful in the formation of catheter shafts, can be used. In one embodiment, the filler material has a relatively low Shore durometer hardness, e.g., of about 40 D to about 73 D. The filler material is preferably the same as or at least compatible with (i.e., fusion bondable to) the polymeric materials forming the outer surfaces of the proximal portions of the inner and outer tubular members to thereby bond the surfaces together. Preferably, a separate adhesive is not used at the rapid exchange junction to bond the inner and outer tubular members together, which are instead fusion bonded together with the polymeric filler material therebetween.

The balloon catheter of the invention can be configured for a variety of applications including coronary or peripheral dilatation, stent or graft delivery, drug delivery, and the like. In one preferred embodiment, the balloon catheter has a sufficiently low profile to allow for use of two of the balloon catheters together, in a procedure commonly referred to as a kissing balloon procedure. A variety of suitable stents can be used with the balloon catheter of invention, which generally comprise expandable tubular members [for details of stent design, see for example U.S. Pat. No. 5,507,768 (Lau et al.) and U.S. Pat. No. 5,458,615 (Klemm et al.), incorporated by reference herein in their entireties].

The catheter of the invention has a low profile, kink resistant rapid exchange junction providing a robust guidewire exit notch. The thin walled, coil reinforced inner tubular member provides excellent flexibility and collapse resistance, and breakthrough of the coil is avoided, due at least in part to the use of a crescent shaped mandrel during assembly and to the polymeric filler material on the proximal portion of the inner tubular member. Thus, the integrity of the catheter lumens is maintained throughout assembly and use of the catheter. These and other advantages of the invention will become more apparent from the following detailed description and exemplary drawings.

DETAILED DESCRIPTION OF THE INVENTION

Figure 1:
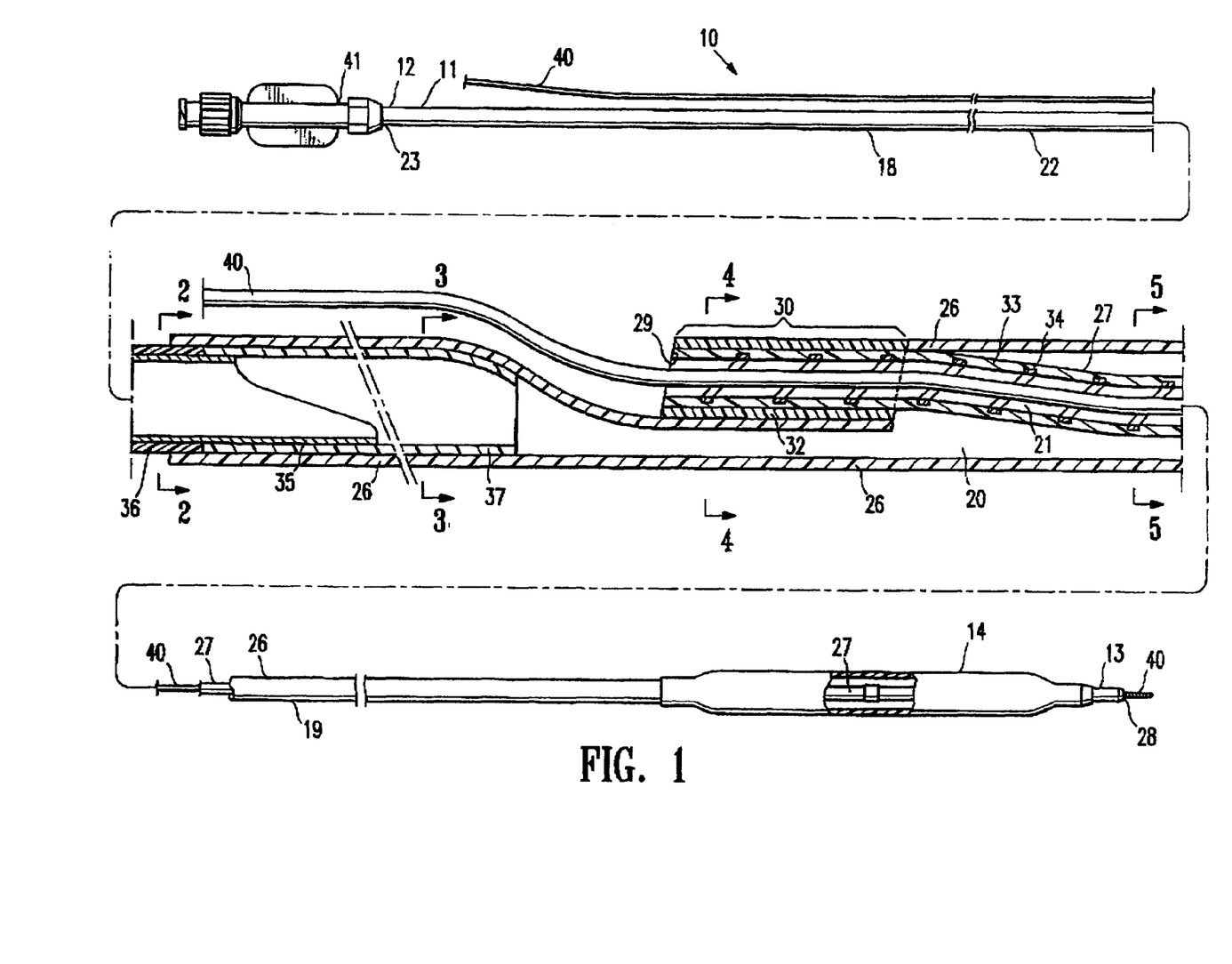
FIG. 1 is an elevational view, partially in section, of a rapid exchange balloon catheter which embodies features of the invention.
Figure 2:
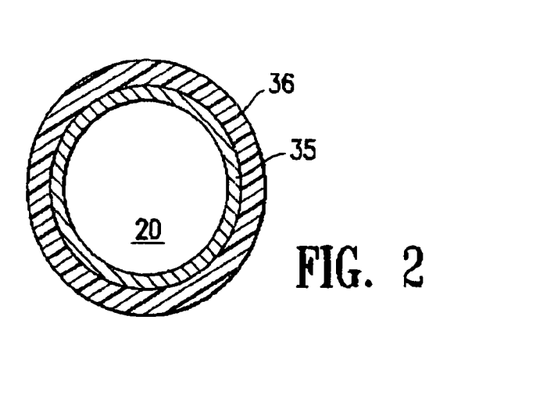
FIGS. 2-5 are transverse cross-sectional views of the catheter shown in FIG. 1, taken along lines 2-2, 3-3, 4-4, and 5-5, respectively.
Figure 3:
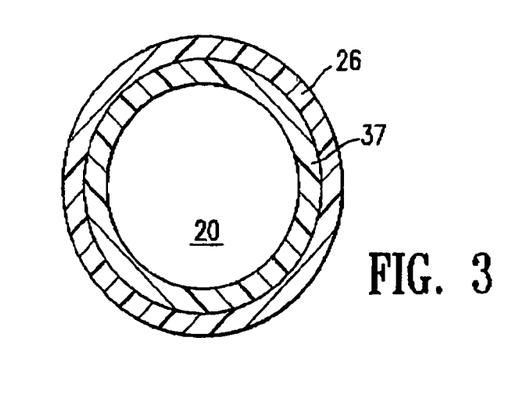

FIG. 1 illustrates rapid exchange type balloon catheter 10 embodying features of the invention. Catheter 10 generally comprises an elongated catheter shaft 11 having a proximal end 12, a distal end 13, a proximal shaft section 18 and a distal shaft section 19 at the distal end of the proximal shaft section, and an inflatable balloon 14 on the distal shaft section. The shaft 11 has an inflation lumen 20, and a guidewire receiving lumen 21. The proximal shaft section 18 comprises a proximal tubular member 22 defining a proximal portion of the inflation lumen 20. In the embodiment illustrated in FIG. 1, the distal end of the proximal tubular member 22 tapers distally to a smaller transverse dimension. The distal shaft section 19 comprises an outer tubular member 26 defining a distal portion of the inflation lumen 20 and an inner tubular member 27 defining the guidewire lumen 21 in fluid communication with a guidewire distal port 28 at the distal end of the catheter, and a guidewire proximal port 29 at the proximal end of the inner tubular member 27, configured to slidably receive guidewire 40 therein. Balloon 14 has a proximal end sealingly secured to the distal end of outer tubular member 26 and a distal end sealingly secured to the distal end of inner tubular member 27, so that its interior is in fluid communication with inflation lumen 20. An adapter 41 at the proximal end of the catheter provides access to the inflation lumen 20. In FIG. 1, the balloon 14 is illustrated prior to being fully inflated. The distal end of catheter 10 may be advanced to a desired region of a patient's body lumen in a conventional manner and balloon 14 inflated to perform a procedure such as dilatation of a stenosed region, and catheter 10 withdrawn or repositioned for another procedure. A rapid exchange junction at the guidewire proximal port 29 is the transition between the single lumen proximal shaft section 18 and the multilumen distal shaft section 19. The inner tubular member 27 extends through (and fills) an opening in a sidewall of the outer tubular member 26. A proximal portion 30 of the inner tubular member 27, located proximal to the sidewall opening, extends in a side-by-side relationship with inflation lumen 20 and is secured to an outer surface of the outer tubular member 26. The proximal portion 30 of the inner tubular member 27 extends along the outer surface of the outer tubular member 26, and is therefore not surrounded by the outer tubular member 26 (which defines the inflation lumen 20), so that the inner tubular member proximal portion 30 defines a portion of the guidewire lumen extending proximally of the sidewall opening of the outer tubular member 26. It should be understood that the terminology "sidewall opening" refers to a break in the sidewall of the outer tubular member 26 through which the inner tubular member extends, so that the "opening" in the sidewall of the outer tubular member 26 is actually filled or closed by the inner tubular member 27 and does not provide fluid communication into the inflation lumen 20 from outside of the catheter. Distal to the proximal portion 30, the inner tubular member 27 transitions to a generally coaxial configuration within the inflation lumen 20 defined by the outer tubular member 26. Although in the illustrated embodiment the inner tubular member 27 is coaxial with a distal portion of the outer tubular member 26, a variety of suitable configurations may be used including a non-coaxial configuration, for example, with all or part of the length of a distal portion of inner tubular member 27 within the inflation lumen 20 being joined to the inner surface of the outer tubular member 26 and not coaxially located therein. The length of the proximal portion 30 of inner tubular member 27 is typically about 0.5 to about 5% of the total length of the inner tubular member, and more specifically in one embodiment is about 2 to about 15 mm.

As best illustrated in FIGS. 2-5, showing transverse cross-sections of the catheter of FIG. 1, taken along lines 2-2, 3-3, 4-4, and 5-5, respectively, the shape of the inflation lumen 20 changes along the length of the catheter. Specifically, inflation lumen 20 transitions from a generally circular shape proximal to the guidewire proximal port 29 (see FIGS. 2 and 3), to a crescent-shape along-side the proximal portion 30 of the inner tubular member 27 (see FIG. 4), and to an annular shape surrounding the guidewire lumen 21 in a distal portion of the distal shaft section 19 (see FIG. 5).

Polymeric filler material 32 around the proximal portion 30 of the inner tubular member 27 is located between the outer surfaces of the inner and outer tubular members 27, 26, preferably bonding the surfaces together. In the embodiment of FIG. 1, the proximal end of the filler material 32 is at the proximal end of the inner tubular member 27. However, the proximal end of the filler material may alternatively extend proximally beyond the proximal end of the inner tubular member 27 to define the guidewire proximal port 29. In the embodiment of FIG. 1, the distal end of the polymeric filler material 32 is at the distal end of the proximal portion 30 of the inner tubular member. The polymeric filler material preferably extends at least along the entire length of the proximal portion 30 of the inner tubular member 27, and in one embodiment has a length which is about 0.5 to about 5% of the total length of the inner tubular member 27. However, in alternative embodiments (not shown), the distal end of the polymeric filler is proximal or distal to the location shown in the embodiment of FIG. 1.

In the embodiment of FIG. 1, the inner tubular member 27 comprises a polymeric tube 33 having a reinforcing coiled member 34 embedded therein. In the illustrated embodiment, the reinforcing coiled member is a ribbon with a flat cross-section and spaced apart turns extending spirally along the entire length of the inner tubular member 27. However, coiled member 34 can have a variety of suitable configurations including stacked turns or a round wire cross-section, and in one embodiment, does not extend to the proximal-most end and/or distal-most end of the inner tubular member 27.

Figures 6, 7:
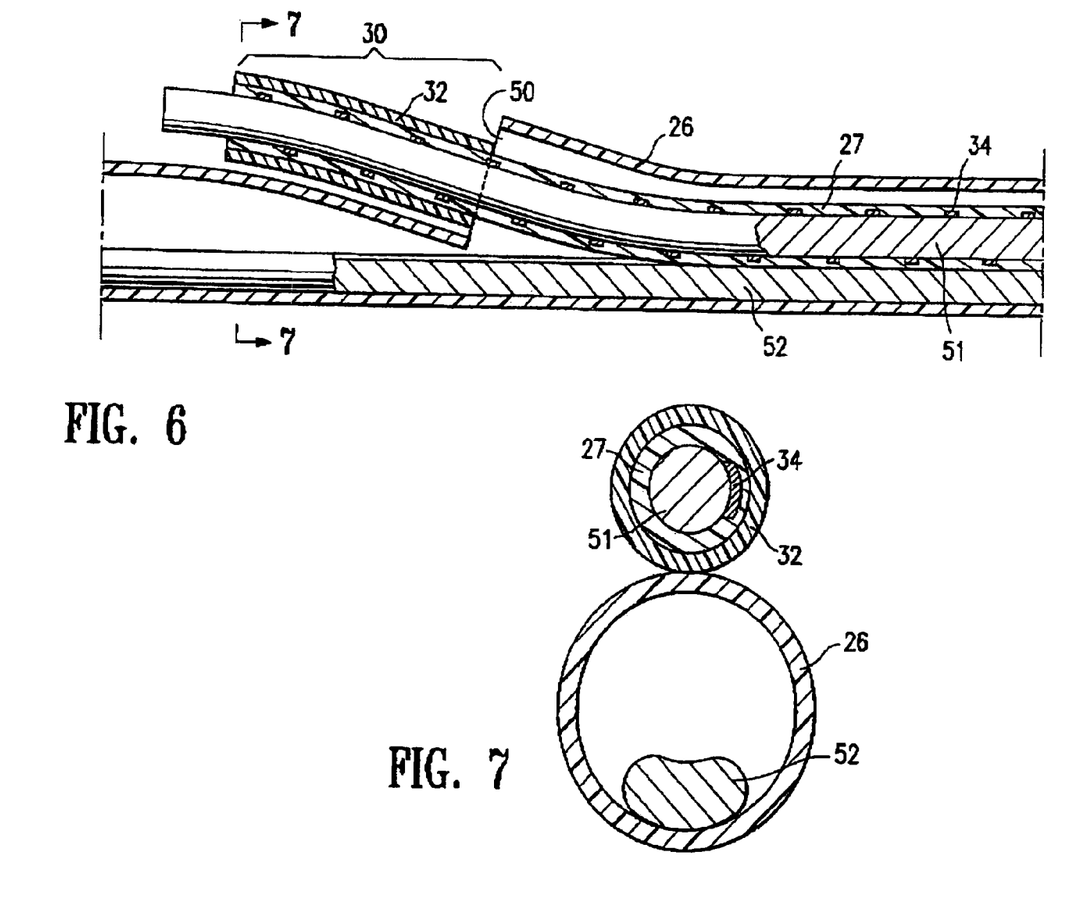
FIG. 6 is an enlarged longitudinal cross-sectional partional view during assembly of the catheter shaft of the catheter of FIG. 1 in a method embodying features of the invention.
FIG. 7 is a transverse cross-sectional view of the assembly shown in FIG. 6, taken along line 7-7.

The polymeric filler material 32 and tubular members 26, 27 are preferably joined together by thermal fusion process, and the catheter shaft assembled, according to a method of making a balloon catheter of the invention. FIG. 6 illustrates an enlarged, longitudinal cross-sectional view of a midportion of shaft 11 of the catheter 10, during assembly thereof. Specifically, the inner tubular member 27 is placed in the lumen of the outer tubular member 26, with the proximal end of the inner tubular member extending through a break 50 in a sidewall of the outer tubular member 26, so that proximal portion 30 of the inner tubular member 27 is positioned alongside an outer surface of the outer tubular member 26. The sidewall break 50 is typically formed by piercing through the wall of the outer tubular member 26 to form a hole therethrough. A polymeric filler material tube 32 is placed around the outer surface of at least the proximal portion 30 of inner tubular member 27. In the embodiment of FIG. 6 the tube 32 extends along a portion of the inner tubular member proximal to the sidewall break 50. The filler material tube 32 of FIG. 6 typically has a length of about 0.2 to about 1.5 cm, preferably about 0.4 to about 0.8 cm, an outer diameter of about 0.6 to about 0.7 mm, and a wall thickness of about 0.02 to about 0.08 mm. The filler material tube 32 preferably has an inner diameter sized to barely fit around the inner tubular member 27. A first assembly mandrel 51 is positioned in the guidewire lumen 21, and a second assembly mandrel 52 is positioned in the inflation lumen 20, to keep the lumens 20, 21 open during bonding together of tubular members 26, 27. As best shown in FIG. 7, illustrating a transverse cross-section of the assembly of FIG. 6, taken along line 7-7, the first assembly mandrel 51 has a round cross-section corresponding to the shape of the guidewire lumen 21, and the second assembly mandrel 52 has a crescent-shaped cross-section. The surface of the mandrel 52 is rounded off at the junctions between the concave and convex surfaces of the mandrel 52.

Figure 4:
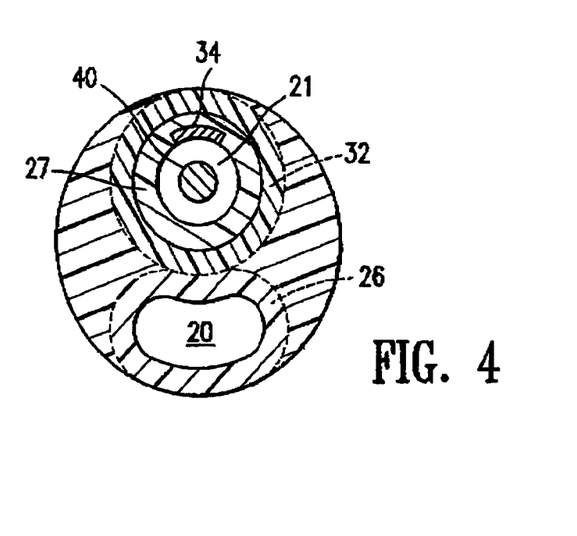
Figure 5:
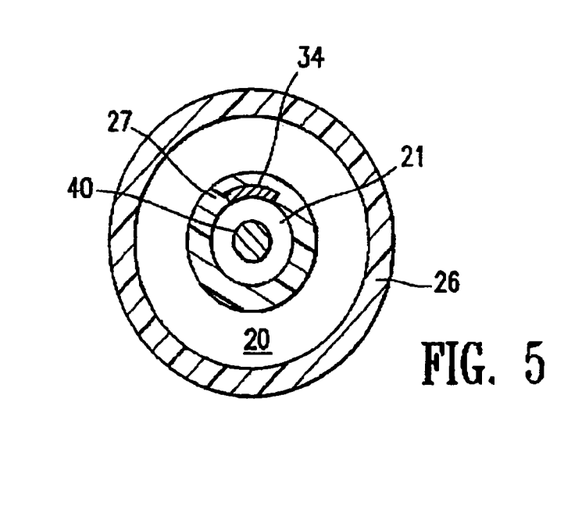

FIG. 6 illustrates the assembly prior to bonding the inner tubular member proximal portion 30 to the outer tubular member 26. Heat, and preferably a radially inward force, are applied to the catheter 10 along either side of the opening 50, to force the inner tubular member proximal portion 30 down onto the outer tubular member 26 and fusion bond the portions of the tubular members 26, 27 together. Typically, a heat shrink tube (not shown) is provided around the outer surface of the catheter shaft (i.e., around the outer and inner tubular members 26, 27) with a length extending along at least the proximal portion 30 of the inner tubular member 27, which shrinks during the heating to apply a radially inward force. The polymeric material of the filler material tube 32 and the tubular member 26 flows as the tubular members are heated and forced together during catheter assembly, filling the space therebetween. The transverse cross section of the resulting bonded region of the shaft shown in FIG. 4 illustrates the outer surfaces of the filler material tube 32 and the outer tubular member 26 in dashed lines to indicate that the polymeric material thereof flows during the bonding. Thus, the polymeric material filling the space around the tubular members 26, 27 (around the dashed lines of tube 32 and tubular member 26) is shown in a different cross hatching to indicate the polymeric filler material of tube 32 and the polymeric material of outer tubular member 26 are both forming the filled-in area defining the outer surface of the shaft after the bonding together of tubular members 26, 27 along the proximal portion 30 of the inner tubular member 27. The concave surface of the mandrel 52 corresponds to the radius of curvature of the outer surface of the inner tubular member 27, so that, as the inner and outer tubular members 26 are forced down onto the concave surface of the mandrel 52, the inner and outer tubular members are not overly thinned during bonding. Consequently, the proximal portion 30 of inner tubular member 27 becomes bonded to the outer surface of the outer tubular member 26. Also, a part of the inner tubular member 27 distal to the sidewall opening 50 becomes bonded to an inner surface of the outer tubular member 26 to complete the sealing of the inflation lumen 20 at the guidewire proximal port 29. Additionally, because the inner tubular member 27 proximal portion 30 is forced down on the outer surface of the outer tubular member 26 during assembly of the catheter shaft, a transition section located proximally adjacent to the proximal end of the inner tubular member is formed along which the outer diameter of the outer tubular member transitions from a first outer diameter section, to a second smaller outer diameter section bonded to the inner tubular member 27 proximal portion 30 (see FIG. 1). In the embodiment of FIG. 1, the section of the outer tubular member 26 located distally beyond the proximal portion of the inner tubular member 27 has a larger outer diameter than the section of the outer tubular member bonded to the proximal portion 30 of the inner tubular member 27.

After the heat bonding, the shrink tubing (not shown) and assembly mandrels 51, 52 are removed, and the resulting rapid exchange junction at the guidewire proximal port 29 preferably has a circular outer surface (see FIG. 4). The thus formed distal shaft section is secured to the distal end of a proximal shaft section, by bonding the distal end of the proximal tubular member 22 to the proximal end of the outer tubular member 26. Additionally, a polymeric reinforcing tube 37 extending distally from the distal end of the proximal tubular member 22, as discussed in more detail below, is fusion bonded to an inner surface of, or at least placed within, the outer tubular member 26 during assembly of the shaft 11. The balloon is bonded to the shaft 11, and the proximal adapter is connected to the proximal end of the shaft 11 to complete assembly of the catheter 10.

In the illustrated embodiment, the proximal tubular member 22 comprises a tubular member 35 formed of a metal, such as stainless steel, with a polymeric jacket 36. Metallic tubular member 35 may alternatively be a high modulus polymer such as PEEK or nylon, or a variety of suitable metallic or polymeric materials. Outer tubular member 26 of the distal shaft section is bonded to the polymeric jacket 36 and/or the metallic tubular member 35. In the embodiment illustrated in FIG. 1, reinforcing polymeric tube 37 is on the distal end of the metallic tubular member 35, extending distally therebeyond in the inflation lumen 20, preferably providing a more gradual stiffness transition between the proximal and distal shaft sections 18, 19. The polymeric reinforcing tube 37 in the embodiment of FIG. 1 is typically positioned in the inflation lumen 20 before the bonding of the inner tubular member 27 proximal portion 30 to the outer tubular member 26. However, the polymeric reinforcing tube 37 can alternatively be positioned in the inflation lumen 20 after the bonding, although the distal end of the polymeric reinforcing tube 37 would typically be proximal to the transition section along which the outer tubular member outer diameter decreases. Similarly, in one embodiment, a distal reinforcing polymeric tube (not shown) may be provided in the crescent-shaped portion of the inflation lumen alongside the proximal portion 30 of the inner tubular member 27 to reinforce the catheter along the guidewire proximal port 29. The distal reinforcing polymeric tube may be adhesively bonded, fusion bonded, or friction fit within the outer tubular member 26.

Although illustrated as a single, solid-walled tube, in alternative embodiments, the polymeric filler material tube 32 is a multi-layered tube having a inner and outer layers. In one presently preferred embodiment, polymeric filler material 32 is a polyamide such as a nylon or a PEBAX, providing improved fusion bonding to a nylon outer tubular member 26, and to a PEBAX outer layer of the inner tubular member 27. Although illustrated as a single layer in FIG. 1, the inner tubular member 27 typically comprises a multi-layered tubular member, which in one embodiment comprises a inner lubricious layer and an outer fusion bondable layer. Similarly, although illustrated as a single tube in FIG. 1, the outer tubular member 26 may comprise multiple tubular members or a multi-layered tubular member, providing desired characteristics such as strength, flexibility, and bondability. Thus, although FIG. 1 illustrates the inner tubular member 27 extending through the sidewall of a polymeric tube forming outer tubular member 26, in alternative embodiments (not shown), the outer tubular member 26 comprises multiple tubes joined lengthwise, end-to-end, and in one embodiment the inner tubular member 27 extends from the end opening of one of these multiple tubes which together form the outer tubular member 26.

A support mandrel (not shown) is typically provided within the inflation lumen 20, preferably formed of a material selected from the group consisting of metals such as stainless steel and nickel titanium alloy, and high modulus polymers such as PEEK and nylon, and reinforced composites thereof. In the embodiment in which proximal tubular member 22 comprises metallic tube 35, the proximal end of the support mandrel is typically secured, for example by soldering, to the distal end section of the metallic tube 35. In one embodiment, the support mandrel extends from the distal end of the proximal tubular member 22 to a location distal to the guidewire proximal port 29 and typically to adjacent to the location along which the inner tubular member 27 becomes coaxial with the outer tubular member 26 in the embodiment of FIG. 1. The support mandrel may be bonded to the shaft 11 along all or only part of its length, and in one embodiment it has a distal section which is free-floating within the distal shaft section.

Figure 8:
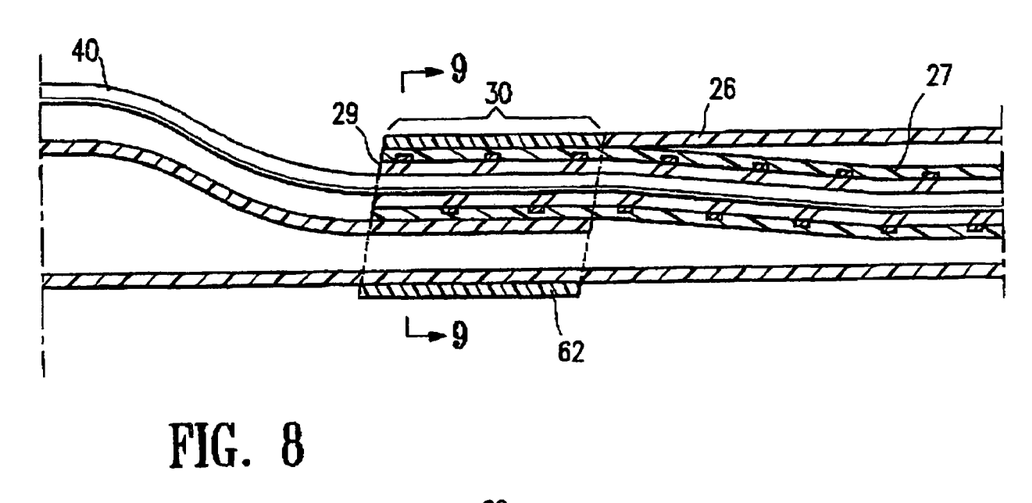
FIG. 8 is an enlarged longitudinal cross section partial view of an alternative embodiment of a balloon catheter embodying features of the invention, having polymeric filler material extending partially around the inner and outer tubular members of the distal shaft section.
Figure 9:
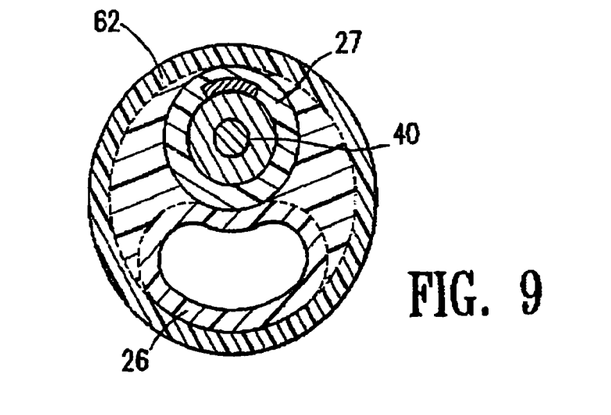
FIG. 9 is a transverse cross-sectional view of the catheter shown in FIG. 8, taken along line 9-9.

FIG. 8 illustrates an enlarged, longitudinal cross section partial view of an alternative embodiment, in which polymeric filler material 62 extends partially around and in contact with the outer surfaces of the inner and outer tubular members 27, 26. Thus, unlike the embodiment of FIG. 1, the filler material tube 62 is configured to be positioned around both the inner and outer tubular members along the proximal portion 30 of the inner tubular member 27 prior to bonding the inner tubular member proximal portion 30 to the outer tubular member 26 (FIG. 8 illustrates the catheter after the heat bonding). The filler material 62 does not extend completely around the circumference of the inner tubular member 27 proximal portion 30, and is thus only partially in contact with the outer surface thereof. FIG. 9 illustrates a transverse cross section of the catheter shown in FIG. 8, taken along line 9-9. As discussed above in relation to the transverse cross section shown in FIG. 4, the polymeric material filling the space around the tubular members 26, 27 (around the dashed lines of tube 62 and tubular member 26) is shown in a different cross hatching to indicate the polymeric filler material of tube 62 and the polymeric material of outer tubular member 26 at least are forming the filled-in area defining the outer surface of the shaft after the bonding together of tubular members 26, 27 along the proximal portion 30 of the inner tubular member 27.

The proximal tubular member 22, inner tubular member 27, and outer tubular member 26 of the catheters of the invention may be formed by conventional techniques, e.g. extruding, from materials already found useful in intravascular catheters such a polyethylene, polyamide, polyesters, and composite materials. The catheter components can be bonded together by heat fusion, adhesive, or by other conventional means.

The catheter shaft will generally have the dimensions of conventional dilatation or stent delivery catheters. The length of the catheter 10, measured from the distal end of the adapter 41 to the distal end of the catheter is about 90 to about 150 cm, typically about 137 cm. The proximal tubular member 22 of the proximal shaft section 18 has a length of about 80 to about 120 cm, typically about 114 cm, an outer diameter (OD) of about 0.3 to about 1.3 mm, and an inner diameter (ID) of about 0.5 to about 1.1 mm. The outer tubular member 26 of the distal shaft section 19 has a length of about 20 to about 35 cm, typically about 25 cm. The section of the outer tubular member proximal to the guidewire proximal port 29 has an OD of about 0.7 to about 0.9 mm, and an ID of about 0.6 to about 0.8 mm. The shaft OD (i.e., combined inner and outer tubular members) along the inner tubular member proximal portion 30 is about 0.8 to about 0.9 mm. The section of the outer tubular member distal to the inner tubular member proximal portion 30 has an OD of about 0.7 to about 0.9 mm, and an ID of about 0.6 to about 0.8 mm. The inner tubular member 27 of the distal shaft section 19 has a length of about 20 to about 35 cm, typically about 25 cm, an OD of about 0.45 to about 0.65 mm, and an ID of about 0.3 to about 0.5 mm. The inner and outer tubular members 27/26 may taper in the distal section to a smaller OD or ID. The balloon 14 may be formed of a variety of suitable compliant, semi- or non-compliant, or hybrid compliant materials depending on the use of the catheter, e.g., dilatation, stent delivery, etc. The length of the balloon 14 is typically about 5 to 50 mm, more specifically about 8 to 40 mm. In an expanded state, the balloon diameter is typically about 1.5 to about 5 mm, more specifically about 1.5 to about 4 mm. The wall thickness will vary depending on the burst pressure requirements and hoop strength of the balloon material.

While the present invention is described herein in terms of certain preferred embodiments, those skilled in the art will recognize that various modifications and improvements may be made to the invention without departing from the scope thereof. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed:
1. A method of making a balloon catheter, comprising:
 a) providing a distal outer tubular member having a sidewall;
 b) forming an opening in said distal outer tubular member by piercing said sidewall;

c) placing an inner tubular member in the outer tubular member and extending a proximal portion of the inner tubular member through said opening in the outer tubular member and along an outer surface of a portion of the outer tubular member proximal to the opening;

d) positioning a polymeric filler material tube at least partially around an outer surface of at least the proximal portion of the inner tubular member;

e) placing a crescent shaped mandrel in the outer tubular member to form a crescent-shaped portion of the outer tubular member lumen along-side the proximal portion of the inner tubular member;

f) applying heat and radially inward force to bond the proximal portion of the inner tubular member to the outer surface of the portion of the outer tubular proximal to the sidewall opening;

g) bonding the distal end of a proximal tubular member to the proximal end of the outer tubular member; and h) bonding a balloon to a distal end of the outer tubular member and to a distal end of the inner tubular member, so that the balloon has an interior in fluid communication with a lumen of the outer tubular member and a lumen of the proximal tubular member.

2. The method of claim 1 wherein the polymeric filler material tube extends between the outer surface of the proximal portion of the inner tubular member and the outer surface of the outer tubular member, such that an inner surface of the polymeric filler material tube is bonded to the outer surface of the proximal portion of the inner tubular member, and an outer surface of the polymeric filler material tube is bonded to the outer surface of the outer tubular member, to thereby bond the inner and outer tubular members together in f).

3. The method of claim 1 wherein the polymeric filler material tube extends around the inner and outer tubular members, so that it partially extends around the inner tubular member and partially extends around the outer surface of the outer tubular member, such that f) includes bonding a first part of an inner surface of the polymeric filler material tube to the outer surface of the proximal portion of the inner tubular member, and a second part of the inner surface of the polymeric filler material tube to the outer surface of the outer tubular member.

* * * * *